United States Patent
Aota et al.

(10) Patent No.: US 8,815,604 B2
(45) Date of Patent: Aug. 26, 2014

(54) MICROCHANNEL CHIP AND METHOD FOR GAS-LIQUID PHASE SEPARATION USING SAME

(75) Inventors: Arata Aota, Kawasaki (JP); Yuko Kihira, Kawasaki (JP); Mari Sasaki, Kawasaki (JP); Takehiko Kitamori, Tokyo (JP); Kazuma Mawatari, Kawasaki (JP)

(73) Assignees: Institute of Microchemical Technology Co., Ltd., Kanagawa (JP); The University of Tokyo, Tokyo (JP); Kanagawa Academy of Science and Technology, Kanagawa (JP)

( * ) Notice: Subject to any disclaimer, the term of this patent is extended or adjusted under 35 U.S.C. 154(b) by 131 days.

(21) Appl. No.: 13/262,103

(22) PCT Filed: Mar. 31, 2010

(86) PCT No.: PCT/JP2010/055797
§ 371 (c)(1),
(2), (4) Date: Mar. 14, 2012

(87) PCT Pub. No.: WO2010/113997
PCT Pub. Date: Oct. 7, 2010

(65) Prior Publication Data
US 2012/0164743 A1 Jun. 28, 2012

(30) Foreign Application Priority Data
Mar. 31, 2009 (JP) ................................. 2009-086805

(51) Int. Cl.
*B01D 53/00* (2006.01)

(52) U.S. Cl.
USPC ............. 436/113; 436/111; 436/106; 422/50; 422/83

(58) Field of Classification Search
CPC ........... B01D 53/00; G01N 1/10; G01N 1/18; G01N 1/00
USPC ............ 436/113, 112, 111, 106, 177; 422/50, 422/83, 527, 86, 68.1
See application file for complete search history.

(56) References Cited

U.S. PATENT DOCUMENTS

| 2006/0046308 A1 | 3/2006 | Yamashita et al. |
| 2008/0017246 A1 | 1/2008 | Tabata et al. |

FOREIGN PATENT DOCUMENTS

| JP | 2004-113874 A | 4/2004 |
| JP | 2005-329364 A | 12/2005 |
| JP | 2006-223118 A | 8/2006 |
| JP | 2008-23418 A | 2/2008 |

OTHER PUBLICATIONS

Hiraku T et al. English Translation of JP document JP 2006 223118, obained on Jul. 18, 2013, pp. 1-14.*

(Continued)

*Primary Examiner* — Christine T Mui
(74) *Attorney, Agent, or Firm* — Birch, Stewart, Kolasch & Birch, LLP

(57) ABSTRACT

A microchannel chip having a microchannel formed in a substrate and a gas-liquid phase separation microchannel whose upper part is covered with a porous film, the gas-liquid phase separation microchannel being connected to the downstream end of the microchannel and having a depth of 10 μm to 100 μm. Also, a gas-liquid phase separation method which is a method for separating a liquid-phase flow from a two-phase flow flowing through a microchannel by removing a gas phase, the two-phase flow composed of the gas phase and the liquid phase, which liquid phase flows in the periphery of the above-described microchannel and which gas phase flows interiorly of the liquid-phase flow.

14 Claims, 3 Drawing Sheets

(56) References Cited

OTHER PUBLICATIONS

Hachiya H et al. English Translation of JP document JP 2005 329364, obtained on Aug. 6, 2013, pp. 1-10.*

International Search Report issued Jul. 13, 2010, in PCT International Application No. PCT/JP2010/055797.

* cited by examiner

MICROCHANNEL CHIP AND METHOD FOR GAS-LIQUID PHASE SEPARATION USING SAME

TECHNICAL FIELD

The present invention relates to a microchannel chip capable of separating a liquid-phase flow from a two-phase flow flowing in a microchannel by removing a gas-phase flow, the two-phase flow being composed of the gas-phase flow and the liquid-phase flow; and a gas-liquid phase separation method using the microchannel chip. The present invention also relates to a microchannel chip for measuring a gaseous test substance and a method of measuring a gaseous test substance.

BACKGROUND ART

In order to reduce the percent defective, semiconductor devices are manufactured in a clean room where dust and the like are present in an extremely small amount. It is required that the air inside such clean room be free from not only dust, but also ammonia. In cases where the air inside the clean room contains ammonia even in a low concentration of several ppb, the accuracy of ultra-fine process-patterning is deteriorated and the percent defective is increased. Therefore, the ammonia concentration of the air inside the clean room must be monitored at all times.

At present, the ammonia concentration of the air inside a clean room is determined by passing the air in the clean room through about 100 mL of a collection solution at a prescribed flow rate using a pump to collect ammonia in the air into the collection solution, which is then transferred to an analysis center where ammonia in the collection solution is quantified.

However, this method requires about 3 days from the start of the measurement to acquisition of analytical result, including the time required for transferring the sample to an analysis center; therefore, prompt action cannot be taken even when the ammonia concentration becomes high. In addition, the ammonia detection limit of this method is about 50 ppb, which is not sufficient.

It is demanded to develop a method of measuring the ammonia concentration in the air, which does not require transferring a sample to an analysis center and is capable of performing a measurement on site in a clean room in a short period of time, preferably in about 20 minutes, and whose measurement sensitivity is in the order of 1 ppb.

The present inventors developed a method of measuring the ammonia concentration in the air using a microchannel chip (Non-patent Document 1). In this method, an air containing ammonia, which is a test sample, and a collection solution are introduced into a microchannel where a gas-liquid two-phase flow is formed and ammonia is extracted from the gas phase into the liquid phase. The two-phase flow is allowed to pass through the microchannel having a hole of 2 mm in diameter on the top and the gas phase is discharged to convert the two-phase flow to a liquid-phase flow. Then, to this liquid-phase flow, a coloring solution and oxidizing solution for ammonia analysis are introduced to color the liquid-phase flow, and the color is measured by a thermal lens microscope (TLM) to determine the ammonia concentration.

According to this method, the ammonia concentration in the air can be measured on site in a period of about 10 minutes in the order of 1 ppb; therefore, the above-described demand can be satisfied.

However, in this method, the measurement reproducibility is low and the coefficient of variation (CV) of the measured values is 20%. Therefore, it is demanded to develop a measurement method having a higher reproducibility.

PRIOR ART DOCUMENTS

Non-Patent Documents

[Non-patent Document 1] The 69th Annual Meeting of the Japan Society for Analytical Chemistry (JSAC) Abstract, p. 31, 2008, JSAC

SUMMARY OF THE INVENTION

Problems to be Solved by the Invention

An object of the present invention is to provide a method of measuring a liquid-soluble gas such as ammonia with good reproducibility and high sensitivity; a gas-liquid phase separation method used for the same; and a microchannel chip for the same.

Means for Solving the Problems

The present inventors intensively studied to discover that the low reproducibility in the method according to Non-patent Document 1 is attributed to unstable gas-liquid phase separation in the microchannel. Further, the present inventors intensively studied a method by which measurement results can be obtained with good reproducibility to discover that, in a microchannel for performing gas-liquid phase separation, by setting the microchannel depth within a specific range and covering the upper part of the microchannel with a porous film which can allow gas to pass therethrough, gas-liquid phase separation can be performed more sufficiently, thereby completing the present invention.

That is, the present invention provides a microchannel chip which comprises a microchannel formed in a substrate and a gas-liquid phase separation microchannel whose upper part is covered with a porous film, the gas-liquid phase separation microchannel being connected to the downstream end of the microchannel and having a depth of 10 µm to 100 µm.

Further, the present invention provides a gas-liquid phase separation method for separating a liquid-phase flow from a two-phase flow flowing through a microchannel by removing a gas phase, the two-phase flow being composed of the gas phase and the liquid phase, which liquid phase flows in the periphery of the above-described microchannel and which gas phase flows interiorly of the liquid-phase flow, the gas-liquid separation method comprising: allowing the above-described two-phase flow to flow through the above-described microchannel in the above-described microchannel chip according to the present invention; leading the two-phase flow to the above-described gas-liquid phase separation microchannel to allow the two-phase flow to flow through this region; and thereby discharging the above-described gas-phase flow to the outside from the above-described gas-liquid phase separation microchannel via the above-described porous film.

Further, the present invention provides a microchannel chip for measuring a gaseous test substance which comprises:

a sample gas introduction microchannel from which a sample gas containing a gaseous test substance soluble to a collection solution is introduced;

a collection solution introduction microchannel from which the above-described collection solution is introduced;

a gas extraction microchannel arranged in the downstream of the junction between the above-described sample gas introduction microchannel and the above-described collection solution introduction microchannel, through which gas extraction microchannel a two-phase flow composed of a liquid-phase flow flowing in the periphery of the above-described gas extraction microchannel and a gas-phase flow flowing interiorly of the liquid phase flow flows;

a gas-liquid phase separation microchannel whose upper part is covered with a porous film, the gas-liquid phase separation microchannel being connected to the downstream end of the gas extraction microchannel and having a depth of 10 μm to 100 μm; and a test substance-measuring microchannel connected to the downstream of the gas-liquid phase separation microchannel, in which test substance-measuring microchannel the liquid-phase flow remaining after the two-phase flow passes through the gas-liquid phase separation microchannel and the gas-phase flow is discharged via the above-described porous film flows; and the test substance contained in the liquid-phase flow is measured.

Further, the present invention provides a method of measuring a gaseous test substance, which comprises the steps of:

introducing the above-described sample gas to the above-described sample gas introduction microchannel of the above-described microchannel chip according to the present invention;

introducing the above-described collection solution to the above-described collection solution introduction microchannel;

collecting the above-described test substance contained in the above-described sample gas into the above-described collection solution by allowing the above-described two-phase flow composed of the above-described sample gas and the above-described collection solution to flow through the above-described gas extraction microchannel;

converting the above-described two-phase flow to a liquid-phase flow by allowing the two-phase flow to flow through the above-described gas-liquid phase separation microchannel to discharge the gas-phase flow to the outside via the above-described porous film; and measuring the above-described test substance contained in the thus obtained liquid-phase flow.

Effects of the Invention

By the present invention, a novel gas-liquid phase separation method capable of stably performing sufficient gas-liquid phase separation in a microchannel and a microchannel chip therefor were provided. By applying the gas-liquid separation method according to the present invention to the method described in Non-patent Document 1 or the like where a test gas is measured using a microchannel, a test gas can be measured in a short period of time with high sensitivity and good reproducibility.

DESCRIPTION OF SYMBOLS

Figure 1:
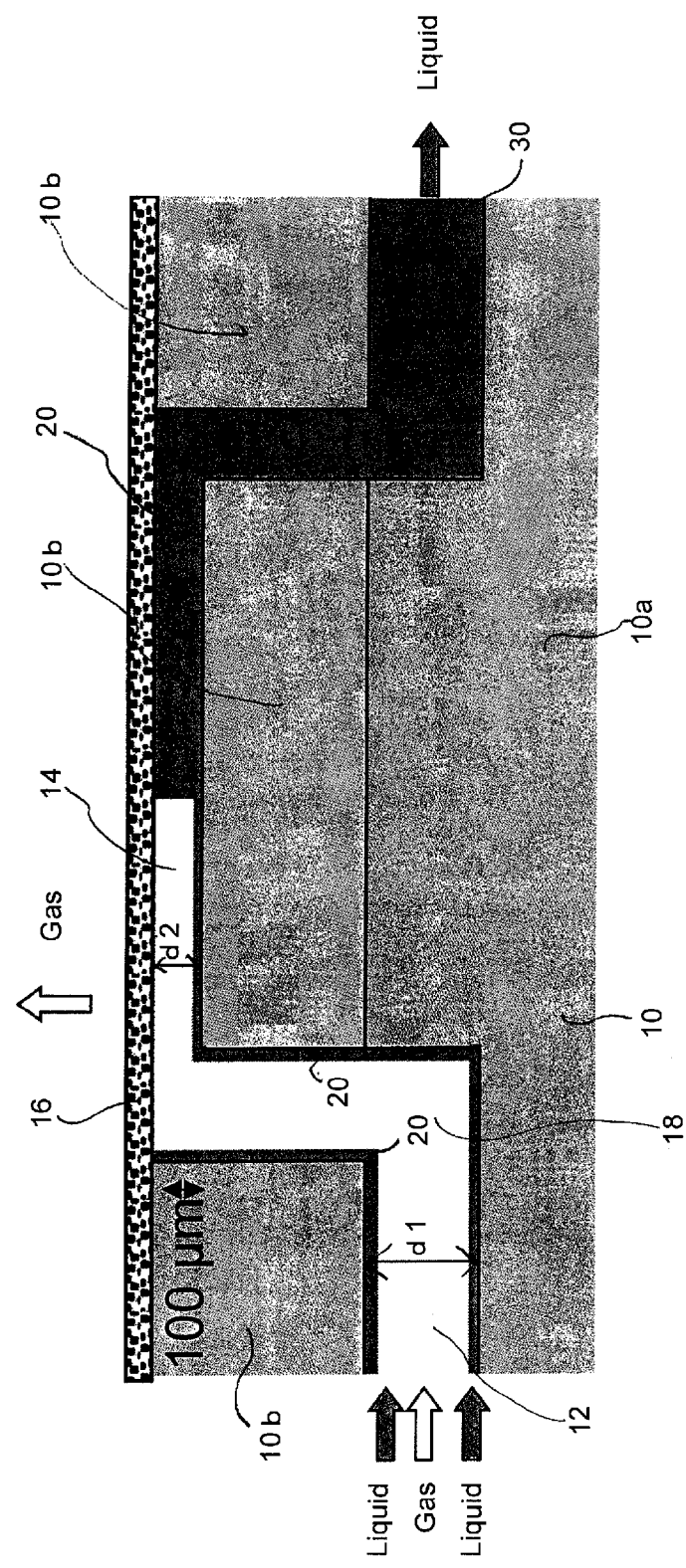
FIG. 1 is a schematic cross-sectional view showing an embodiment of the microchannel chip according to the present invention which comprises a gas-liquid phase separation microchannel.

10: Substrate
12: Microchannel
14: Gas-liquid phase separation microchannel
16: Porous film
18: Gas-phase flow
20: Liquid-phase flow
22: Microchannel chip for measuring a liquid-soluble gaseous test substance
24: Sample gas introduction microchannel
26: Collection solution introduction microchannel
28: Test substance
30: Test substance-measuring microchannel
34: Oxidizing solution introduction microchannel
36: Coloring solution introduction microchannel

MODE FOR CARRYING OUT THE INVENTION

Microchannel chips per se in which a microchannel is formed in a substrate are capable of efficiently performing a variety of chemical reactions and have already been widely used. In many cases, the microchannel is provided in the form of a groove in a substrate made of glass, plastic, metal or the like, and the upper part of the microchannel is covered with a flat plate such as a glass plate. Usually, the microchannel has a substantially semicircular or semielliptical cross-sectional shape. Needless to say, the cross-sectional shape of the microchannel is not restricted to semicircle or semiellipse, and it may be rectangular, circular, elliptical or other arbitrary shape. The microchannel has a width of usually about 10 μm to 600 μm, preferably about 100 μm to 500 μm, and a depth of usually about 5 μm to 300 μm, preferably about 50 μm to 200 μm.

The gas-liquid phase separation microchannel in the microchannel chip according to the present invention is a microchannel which is connected to the downstream end of such microchannel formed in a substrate and has a depth of 10 μm to 100 μm, preferably 40 μm to 90 μm, and whose upper part is covered with a porous film.

The preferred embodiment of the microchannel chip according to the present invention will now be described referring to the drawings. FIG. 1 is a schematic cross-sectional view showing an embodiment of the microchannel chip according to the present invention which comprises a gas-liquid phase separation microchannel. FIG. 1 is a lateral cross-sectional view of the substrate in which a microchannel is formed. A microchannel 12 is formed inside a substrate 10. In the embodiment shown in the drawing, the depth of the microchannel 12 is d1. To the downstream end of the microchannel 12, a gas-liquid phase separation microchannel 14 is connected. The depth of this microchannel is d2 and as shown in the drawing, d2 is smaller than d1. The width (width perpendicular to the drawing plane of FIG. 1) of the microchannel 12 and that of the gas-liquid phase separation microchannel 14 may be the same or different. Further, the length of the gas-liquid phase separation microchannel 14 is not particularly restricted; however, it is usually about 0.5 cm to 5 cm, preferably about 1 cm to 2 cm.

The upper part of the gas-liquid phase separation microchannel 14 is covered with a porous film 16. The porous film 16 is not particularly restricted as long as it can allow gas to pass therethrough; however, the porous film 16 has an average pore size of usually about 0.1 μm to 2.0 μm, preferably about 0.4 μm to 1 μm, and a porosity of about 50% to 90%, preferably about 70% to 80%. Further, the thickness of the porous film is not particularly restricted; however, it is usually 10 μm to 200 μm, preferably about 50 μm to 100 μm. The material of the porous film 16 is not particularly restricted as long as it can allow gas to pass therethrough; however, it is preferred that the porous film 16 be made of a hydrophobic material. Here, "porous film made of a hydrophobic material" refers to a porous film which has hydrophobicity at a level where water does not infiltrate to the other side even when the film comes into contact with water. Examples of preferred hydrophobic material forming the porous film include polytetrafluoroethylene (trade name: Teflon (registered trademark)), perfluoroalkoxy ethylene, polyethylene, polypropylene, polyvinyl alcohol and nylon. Teflon (registered trademark) which can be preferably used as the porous film 16 is commercially available (model: T080A025A; manufactured by ADVANTEC); therefore, a commercial product can be preferably used.

In the embodiment shown in FIG. 1, the microchannel chip is constituted by two substrates, that is, a bottom substrate 10a and an upper substrate 10b. The microchannel 12 is formed in the form of a groove on the upper surface of the bottom substrate 10a and the gas-liquid phase separation microchannel 14 is formed in the form of a groove on the upper surface of the upper substrate 10b. A vertical canal is formed in the upper substrate 10b to connect the microchannel 12 to the upstream end of the gas-liquid phase separation microchannel 14, so that the downstream end of the microchannel 12 and the upstream end of the gas-liquid phase separation microchannel 14 are connected. Further, the bottom surface of the upper substrate 10b covers the upper part of the microchannel 12 to close the microchannel 12. By adopting such constitution, the microchannel chip according to the present invention can be easily prepared. It should be noted here, however, that the constitution may be one in which the microchannel 12 and the gas-liquid phase separation microchannel 14 are formed in the same substrate with the upper part of the microchannel 12 being covered with a flat plate such as a glass plate and the above-described porous film 16 covering only the upper part of the gas-liquid phase separation microchannel 14.

Figure 2:
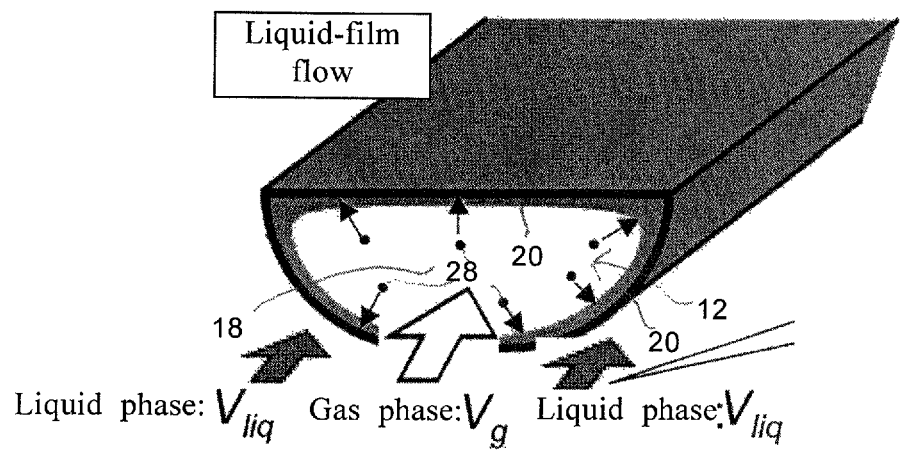
FIG. 2 is a drawing which schematically illustrates a two-phase flow flowing in the microchannel.

By using the microchannel chip according to the present invention, a two-phase flow flowing in the microchannel, which is composed of a gas phase and a liquid phase, can be separated into gas and liquid. That is, a two-phase flow can be made into a liquid-phase flow by removing the gas phase from the microchannel. First, in the upstream portion of the microchannel 12, a gas-phase flow and a liquid-phase flow are introduced to the microchannel 12 using a pump (described later). This allows, as schematically shown in FIG. 2, a liquid-phase flow 20 to flow in the form of a film (liquid-film flow) along the inner surface of the microchannel 12 due to the surface tension and a gas-phase flow 18 to flow interiorly of the liquid-film flow (center side). In FIG. 1, the gas-phase flow 18 is represented by the solid-white part and the liquid-phase flow 20 is represented by the dark gray part. A two-phase flow which contains such liquid phase flow 20 and gas-phase flow 18 flowing interiorly thereof flows through the microchannel 12. When this two-phase flow reaches the gas-liquid phase separation microchannel 14, the gas-phase flow 18 is discharged to the outside via the porous film 16 (in FIG. 1, this is represented by an open up-arrow) and the two-phase flow becomes the liquid-phase flow 20 (in FIG. 1, only the liquid-phase flow 20 is shown in the right half of the gas-liquid phase separation microchannel 14). In this case, it is preferred that the depth d2 of the gas-liquid phase separation microchannel 14 be smaller than the depth d1 of the microchannel 12 since the gas phase becomes more easily discharged. In a further downstream, the liquid-phase flow 20 is subjected to a measurement utilizing an arbitrary chemical reaction.

According to the above-described gas-liquid phase separation method of the present invention, gas-liquid phase separation can be stably performed over a period of 24 hours or longer. In contrast, in the method according to Non-patent Document 1 where the gas phase is discharged from a hole of 2 mm in diameter, the longest continuous performance of gas-liquid phase separation has been mere 8 hours. Further, in the method according to Non-patent Document 1, since the liquid collects in a large volume, the separated liquid cannot be smoothly transferred to the downstream. However, by using a porous film and preferably making the depth of the gas-liquid phase separation microchannel small, the liquid collection volume is reduced and the liquid transfer becomes smooth. Moreover, in the method according Non-patent Document 1, the pressure condition for phase separation is narrow and phase separation may not be attained due to pump malfunction or a change in the humidity/temperature. According to the method of the present invention, the pressure condition in the microchannel under which phase separation can be performed is broadened and a phase separation method which is strong against disturbance and changes in the ambient environment is attained.

The above-described gas-liquid phase separation method according to the present invention can be utilized to measure a liquid-soluble gaseous test substance such as ammonia. A preferred embodiment will now be described referring to the drawings.

Figure 3:
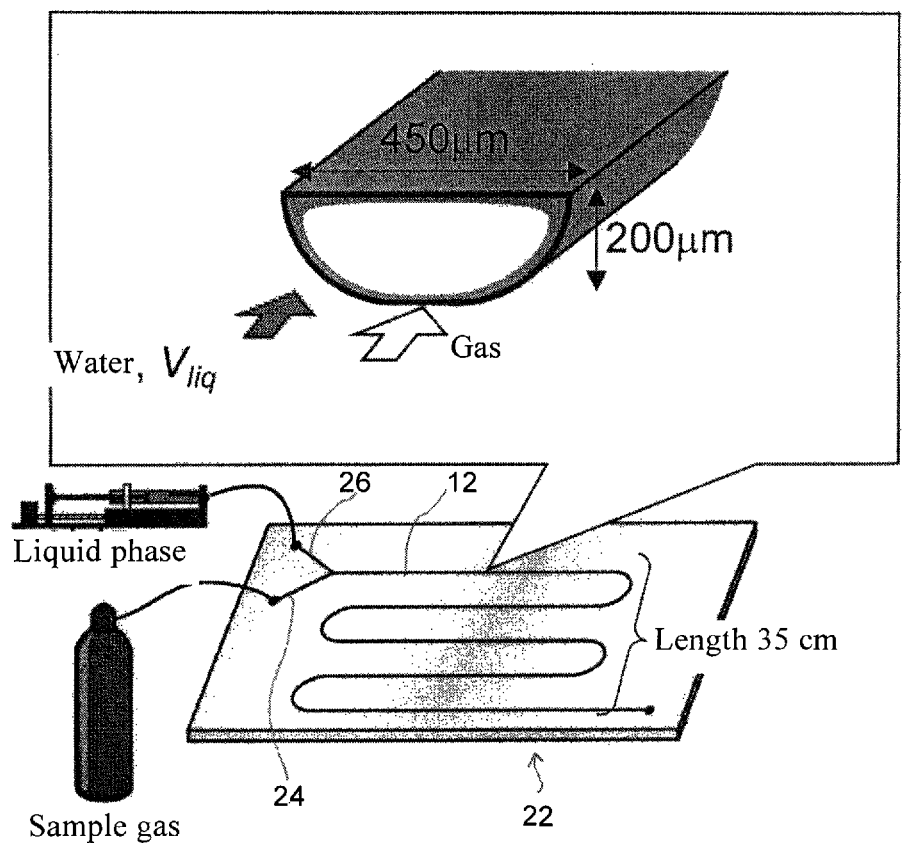
FIG. 3 is a drawing which schematically illustrates the microchannel chip according to the present invention for measuring a liquid-soluble gaseous test substance.

A microchannel chip 22 (FIG. 3) for measuring a liquid-soluble gaseous test substance comprises a sample gas introduction microchannel 24 from which a sample gas containing a gaseous test substance soluble to a collection solution is introduced and a collection solution introduction microchannel 26 from which the above-described collection solution is introduced. The sample gas introduction microchannel 24 and the collection solution introduction microchannel 26 merge into the above-described microchannel 12. As schematically shown in FIG. 2, in the microchannel 12, a gaseous test substance 28 contained in the gas-phase flow 18 is extracted into the liquid-phase flow 20 composed of the collection solution (arrows in FIG. 2); therefore, the microchannel 12 functions as a gas extraction microchannel. As described in the above, a two-phase flow composed of the liquid-phase flow 20 flowing along the inner surface of the microchannel and the gas-phase flow 18 flowing interiorly thereof is formed. In this two-phase flow condition, the test substance 28 contained in the gas-phase flow 18 is efficiently extracted into the liquid-phase flow 20 composed of the collection solution. The length of the gas extraction microchannel 12 is not particularly restricted; however, it is usually about 1 cm to 60 cm, preferably about 30 cm to 40 cm.

As described in the above, the downstream end of the gas extraction microchannel 12 is connected to the gas-liquid phase separation microchannel 14 and the two-phase flow is separated into gas and liquid in the gas-liquid phase separation microchannel 14 in the above-described manner to become a liquid-phase flow.

Connected to the downstream of the gas-liquid phase separation microchannel 14 is a test substance-measuring microchannel 30 (FIG. 1) in which the liquid-phase flow 20 remaining after the two-phase flow passes through the gas-liquid phase separation microchannel 14 and the gas-phase flow 18 is discharged via the porous film 16 flows and the test substance 28 (FIG. 2) contained in the liquid-phase flow 20 is measured. The size of the test substance-measuring microchannel 30 may be any ordinary size as described in relation to the microchannel 12 and may be the same as or different from that of the microchannel 12. The length of the test substance-measuring microchannel 30 is selected as appropriate in accordance with the chemical reaction performed therein; however, it is usually about 1 cm to 80 cm, preferably about 35 cm to 55 cm.

To the test substance-measuring microchannel 30, one or more microchannels for introducing a reagent required for the measurement of the test substance may also be connected. In cases where the test substance is ammonia, for example, the measurement thereof can be performed by indophenol method in which an oxidizing solution such as hypochlorite (e.g. sodium hypochlorite) and a coloring solution such as phenol are reacted with ammonia to produce a blue dye. The chemical reaction scheme of the indophenol method is as follows.

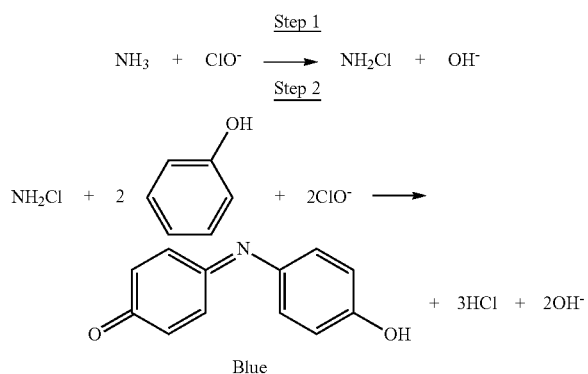

Therefore, in cases where the test substance is ammonia and it is allowed to generate color by an indophenol method to perform colorimetry, a microchannel from which an oxidizing solution is introduced and a microchannel from which a coloring solution is introduced are connected to the test substance-measuring microchannel 30.

After performing a chemical reaction(s) required for the measurement in the test substance-measuring microchannel 30, the liquid-phase flow 20 is discharged to the outside of the chip from a downstream part or the downstream end of the test substance-measuring microchannel 30 and the test substance is then measured. It is noted here that the term "measure" used herein encompasses detection, quantification and semiquantification. In cases where the test substance, ammonia, is subjected to calorimetry by the above-described indophenol method, for example, the generated blue dye can be quantified by observing a downstream part of the test substance-measuring microchannel 30 under a thermal lens microscope (TLM). A thermal lens microscope is a device in which a substance in a microchannel is irradiated with two laser beams called excitation beam and probe beam and the change in the refractive index of the liquid caused by the laser irradiation (the refractive index changes with the temperature of the liquid) and the change in the probe beam intensity caused by modulation of the excitation beam are simultaneously detected to quantify the substance in the microchannel with high sensitivity. Such thermal lens microscope is already commercially available (Institute of Microchemical Technology Co., Ltd.); therefore, a commercial product can be preferably used.

In cases where the concentration of ammonia contained in the air is measured using the above-described microchannel chip, a sample air for which the ammonia concentration is measured is injected into the sample gas introduction microchannel 24 and at the same time, water is injected as a collection solution into the collection solution introduction microchannel 26. The injection rate of the sample gas is not particularly restricted; however, it is usually about 10 mL/min to 1,000 mL/min, preferably about 50 mL/min to 150 mL/min. The water injection rate is not particularly restricted; however, it is usually about 0.5 µL/min to 10 µL/min, preferably about 1 µL/min to 5 µL/min. The sample gas introduction microchannel 24 and the collection solution introduction microchannel 26 merge into the gas extraction microchannel 12 and this is where the above-described two-phase flow is formed and ammonia contained in the sample air is extracted into water, which the collection solution. Since the solubility of ammonia in water is extremely large, 100% of ammonia is extracted as long as the amount thereof is at a level which is contained in the room air. As described in the above, the air flow is discharged to the outside via the porous film 16 while passing through the gas-liquid phase separation microchannel 14 which follows the gas extraction microchannel 12, and the two-phase flow becomes the liquid-phase flow (water flow) 20. To the test substance-measuring microchannel 30 following the gas-liquid phase separation microchannel 14, the above-described oxidizing solution introduction microchannel and coloring solution introduction microchannel are connected, and from these microchannels, the above-described oxidizing solution and coloring solution are introduced, respectively (see FIG. 4 described below). The above-described chemical reactions of the indophenol method take place in the test substance-measuring microchannel 30 and the generated blue dye is quantified under the above-described thermal lens microscope.

As concretely described in the following examples, according to this method, detection limit concentration of ammonia can be achieved in the order of 1 ppb. Further, according to this method, since the discharge of the air flow is more completely performed as compared to the method described in Non-patent Document 1, the variation in the values measured by a thermal lens microscope becomes small and the reproducibility is high.

The present invention will now be described more concretely by way of examples thereof. However, the present invention is not restricted to the following examples.

EXAMPLES

Example 1

Figure 4:
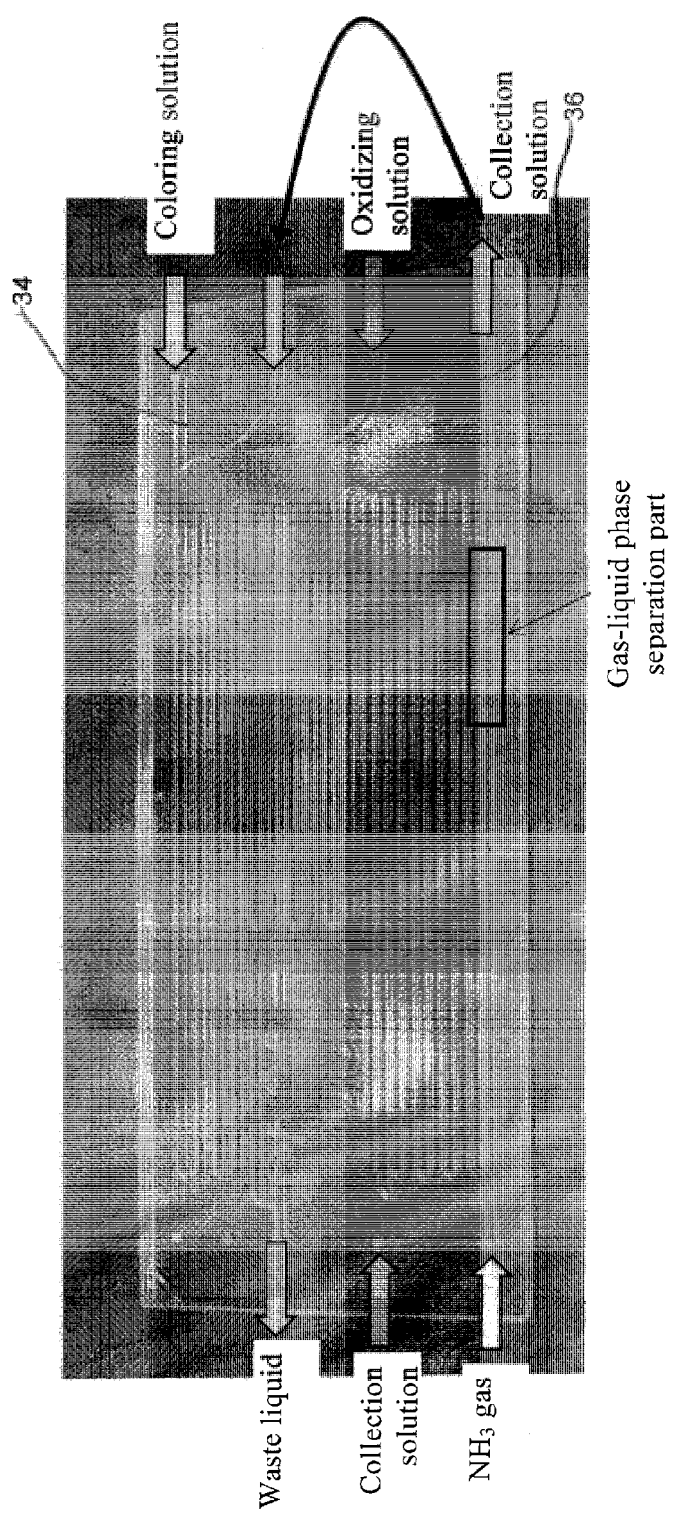
FIG. 4 is a schematic plan view of a microchannel chip which is an example of the present invention.

A microchannel chip having the gas-liquid phase separation microchannel shown in FIG. 1 was prepared. The schematic plan view thereof is shown in FIG. 4. To the test substance-measuring microchannel 30, an oxidizing solution introduction microchannel 34 and a coloring solution introduction microchannel 36 were connected. In the microchannel chip shown in FIG. 4, after allowing a collection solution to which ammonia gas was dissolved to pass through a gas-liquid phase separation part, the collection solution is once led to a tube arranged outside of the chip (indicated by a solid arrow in FIG. 4). The collection solution is then re-introduced to the channel inside the chip and combined with a coloring solution and an oxidizing solution and these are allowed to react in a further downstream of the microchannel. It is noted here that FIG. 4 shows a substrate on which microchannels are formed and that the microchannel of the part enclosed in a rectangle and indicated as "gas-liquid phase separation part" is covered with a Teflon (registered trademark) film. The gas-liquid phase separation microchannel 14 had a semielliptical cross-section of 400 μm in width and 80 μm in depth and all of the other microchannels had a semielliptical cross-section of 500 μm in width and 150 μm in depth. The lengths of the gas extraction microchannel 12, the gas-liquid phase separation microchannel and the test substance-measuring microchannel 30 were 35 cm, 1 cm and 50 cm, respectively. As described in the above referring to FIG. 1, the microchannel chip was prepared by forming the microchannels on the upper surfaces of the respective two glass substrates and laminating these glass substrates.

From the upstream of this gas-liquid phase separation microchannel (indicated as "$NH_3$ gas" in FIG. 4), $NH_3$ gas diluted with nitrogen gas and water, which is the collection solution, were introduced at a flow rate of 100 ml/min and 3 μL/min, respectively, and the part of the gas-liquid phase separation microchannel was observed under a microscope. As a result, gas-liquid phase separation was able to be stably performed over a period of not less than 24 hours and the liquid flow after the gas-liquid phase separation was smooth as well.

Comparative Example 1

A microchannel chip was prepared in the same manner as in Example 1 except that an air hole of 2 mm in diameter was formed on the upper part of the microchannel in place of the gas-liquid phase separation microchannel 14, and the state of gas-liquid phase separation was observed under a microscope in the same manner as described in the above. As a result, continuous gas-liquid phase separation was attained for only 8 hours at best. In addition, there was observed a case where the liquid flow after the gas-liquid phase separation was not smooth.

The invention claimed is:

1. A microchannel chip, which comprises a microchannel formed in a substrate and a gas-liquid phase separation microchannel whose upper part is covered with a porous film, said gas-liquid phase separation microchannel being connected to the downstream end of said microchannel, wherein
a depth of the microchannel is 150 μm to 200 μm,
a depth of the gas-liquid phase separation microchannel is 10 μm to 100 μm, and
said porous film is a polytetrafluoroethylene film having an average pore size of 0.1 μm to 2.0 μm and a porosity of 70% to 80%.

2. The microchannel chip according to claim 1, wherein the depth of said gas-liquid phase separation microchannel is smaller than that of said microchannel.

3. The microchannel chip according to claim 1, wherein said porous film is made of a hydrophobic material.

4. The microchannel chip according to claim 1, wherein said microchannel has a width of 10 μm to 600 μm and a depth of 5 μm to 300 μm.

5. The microchannel chip according to claim 1, wherein said gas-liquid phase separation microchannel has a length of 0.5 cm to 5 cm.

6. A gas-liquid phase separation method for separating a liquid-phase flow from a two-phase flow flowing through a microchannel by removing a gas phase, said two-phase flow being composed of said gas phase and liquid phase, which liquid phase flows in the periphery of said microchannel and which gas phase flows interiorly of said liquid-phase flow, said gas-liquid separation method comprising:

allowing said two-phase flow to flow through said microchannel in the microchannel chip according to claim 1; and
leading said two-phase flow to said gas-liquid phase separation microchannel to allow said two-phase flow to flow through this region, thereby discharging said gas-phase flow to the outside from said gas-liquid phase separation microchannel via said porous film.

7. A microchannel chip for measuring a gaseous test substance, which comprises:
a sample gas introduction microchannel from which a sample gas containing a gaseous test substance soluble to a collection solution is introduced;
a collection solution introduction microchannel from which said collection solution is introduced;
a gas extraction microchannel arranged in the downstream of the junction between said sample gas introduction microchannel and said collection solution introduction microchannel, through which gas extraction microchannel a two-phase flow composed of a liquid-phase flow flowing in the periphery of said gas extraction microchannel and a gas-phase flow flowing interiorly of said liquid-phase flow flows;
a gas-liquid phase separation microchannel whose upper part is covered with a porous film, said gas-liquid phase separation microchannel being connected to the downstream end of said gas extraction microchannel; and
a test substance-measuring microchannel connected to the downstream of said gas-liquid phase separation microchannel, in which test substance-measuring microchannel said liquid-phase flow remaining after said two-phase flow passes through said gas-liquid phase separation microchannel and said gas-phase flow is discharged via said porous film flows; and said test substance contained in said liquid-phase flow is measured, wherein
a depth of the gas extraction microchannel is 150 μm to 200 μm,
a depth of the gas-liquid phase separation microchannel is 10 μm to 100 μm, and
said porous film is a polytetrafluoroethylene film has having an average pore size of 0.1 μm to 2.0 μm and a porosity of 70% to 80%.

8. The microchannel chip according to claim 7, which further comprises at least one reagent introduction microchannel merging with any of said microchannels, said reagent introduction microchannel being used for supplying a reagent required for measuring said test substance.

9. A method of measuring a gaseous test substance, which comprises the steps of:
introducing said sample gas at a rate of 50 mL/min. to 150 mL/min. to said sample gas introduction microchannel of the microchannel chip according to claim 7;
introducing said collection solution at a rate of 1 μL/min. to 5 μL/min. to said collection solution introduction microchannel;
collecting said test substance contained in said sample gas into said collection solution by allowing said two-phase flow composed of said sample gas and said collection solution to flow through said gas extraction microchannel;
converting said two-phase flow to a liquid-phase flow by allowing said two-phase flow to flow through said gas-liquid phase separation microchannel to discharge gas-phase flow to the outside via said porous film; and
measuring said test substance contained in the thus obtained liquid-phase flow.

10. The method according to claim 9, wherein said gaseous test substance is ammonia.

11. The method according to claim 10, wherein said microchannel chip further comprises two said reagent introduction microchannels, from one of which a coloring solution is introduced and from the other of which an oxidizing solution is introduced.

12. The method according to claim 11, wherein ammonia is measured using a thermal lens microscope.

13. A method of measuring a gaseous test substance, which comprises the steps of:
   introducing said sample gas at a rate of 50 mL/min. to 150 mL/min. to said sample gas introduction microchannel of the microchannel chip according to claim 10;
   introducing said collection solution at a rate of 1 μL/min. to 5 μL/min. to said collection solution introduction microchannel;
   collecting said test substance contained in said sample gas into said collection solution by allowing said two-phase flow composed of said sample gas and said collection solution to flow through said gas extraction microchannel;
   converting said two-phase flow to a liquid-phase flow by allowing said two-phase flow to flow through said gas-liquid phase separation microchannel to discharge gas-phase flow to the outside via said porous film; and
   measuring said test substance contained in the thus obtained liquid-phase flow.

14. The method according to claim 13, wherein said gaseous test substance is ammonia.

\* \* \* \* \*